(12) United States Patent
Beckmann et al.

(10) Patent No.: US 11,298,362 B2
(45) Date of Patent: Apr. 12, 2022

(54) COMBINATION THERAPY WITH NOTCH AND CDK4/6 INHIBITORS FOR THE TREATMENT OF CANCER

(71) Applicant: Eli Lilly and Company, Indianapolis, IN (US)

(72) Inventors: Richard Paul Beckmann, Indianapolis, IN (US); Bharvin Kumar Patel, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 699 days.

(21) Appl. No.: 16/093,123

(22) PCT Filed: Apr. 5, 2017

(86) PCT No.: PCT/US2017/026134
§ 371 (c)(1),
(2) Date: Oct. 11, 2018

(87) PCT Pub. No.: WO2017/180389
PCT Pub. Date: Oct. 19, 2017

(65) Prior Publication Data
US 2021/0213029 A1 Jul. 15, 2021

Related U.S. Application Data

(60) Provisional application No. 62/321,311, filed on Apr. 12, 2016.

(51) Int. Cl.
| | |
|---|---|
| *A61K 31/55* | (2006.01) |
| *A61P 35/00* | (2006.01) |
| *A61P 35/04* | (2006.01) |
| *A61K 31/506* | (2006.01) |
| *A61K 31/4745* | (2006.01) |

(52) U.S. Cl.
CPC .......... *A61K 31/55* (2013.01); *A61K 31/4745* (2013.01); *A61K 31/506* (2013.01); *A61P 35/00* (2018.01); *A61P 35/04* (2018.01)

(58) Field of Classification Search
None
See application file for complete search history.

(56) References Cited

U.S. PATENT DOCUMENTS

| | | | |
|---|---|---|---|
| 8,569,286 | B2 | 10/2013 | Hipskind et al. |
| 10,555,951 | B2 | 2/2020 | Benhadji et al. |
| 10,688,104 | B2 | 6/2020 | Bender et al. |
| 2005/0187179 | A1 | 8/2005 | Miele et al. |
| 2013/0029972 | A1 | 1/2013 | Hipskind |
| 2018/0104254 | A1 | 4/2018 | Benhadji et al. |
| 2019/0192531 | A1 | 6/2019 | Bender et al. |
| 2019/0209581 | A1 | 7/2019 | Benhadji et al. |
| 2019/0231794 | A1 | 8/2019 | Benhadji et al. |
| 2020/0289565 | A1 | 9/2020 | Green et al. |

FOREIGN PATENT DOCUMENTS

| | | |
|---|---|---|
| CN | 102 085 372 | 6/2011 |
| CN | 102 264 725 | 11/2011 |
| CN | 103 282 364 | 9/2013 |
| WO | WO 1998/28268 | 7/1998 |
| WO | WO 2007/005874 | 1/2007 |
| WO | WO 2008/112249 | 9/2008 |
| WO | WO 2009/023453 | 2/2009 |
| WO | WO 2010/075074 | 7/2010 |
| WO | WO 2011/060051 | 5/2011 |
| WO | WO 2012/097039 | 7/2012 |
| WO | WO 2013/016081 | 1/2013 |
| WO | WO 2014/193898 | 12/2014 |
| WO | WO 2015/026634 | 2/2015 |
| WO | WO 2015/193352 | 12/2015 |
| WO | WO 2016/040880 | 3/2016 |
| WO | WO 2016/164580 | 10/2016 |
| WO | WO 2016/168014 | 10/2016 |
| WO | WO 2017/180385 | 10/2017 |
| WO | WO 2017/180389 | 10/2017 |
| WO | WO 2017/200969 | 11/2017 |
| WO | WO 2018/044662 | 3/2018 |
| WO | WO 2018/071307 | 4/2018 |
| WO | WO 2018/044662 | 9/2018 |
| WO | WO 2018/201056 | 11/2018 |

(Continued)

OTHER PUBLICATIONS

VanArsdale et al., Molecular Pathways: Targeting the Cyclin D-CDK4/6 Axis for Cancer Treatment. Clinical Cancer Research, 2015, 21, 2905-2910.*
U.S. Appl. No. 16/093,117, filed Oct. 11, 2018, by Patel et al.
U.S. Appl. No. 16/301,360, filed Nov. 13, 2018, by Bender et al.
U.S. Appl. No. 16/328,267, filed Feb. 25, 2019, by Benhadji et al.
Anonymous, "FS25 Peripheral T-Cell Lymphoma Facts | p. 1 Revised," Leukemia & Lymphoma Society (2014) Retrieved on https://www.lls.org/sites/default/files/file_assets/peripheraltcell-lymphomafacts.pdf.
Anonymous, "Notch Inhibitor Shows Modest Efficacy," Cancer Discovery (2016) pp. 1-3. Retrieved on URL:http://cancerdiscovery.aacrjournals.org/content/early/2016/12/13/2159-8290.CD-NB2016-159.
Bell et al., "Expression and significance of Notch signaling pathway in salivary adenoid cystic carcinoma," Annals of Diagnostic Pathology, (2014) 18: 10-13.

(Continued)

*Primary Examiner* — Po-Chih Chen
(74) *Attorney, Agent, or Firm* — Morrison & Foerster, LLP

(57) ABSTRACT

Medicaments for use in treating acute myelogenous leukemia, chronic myelogenous leukemia, breast cancer, ovarian cancer, malignant melanoma, lung cancer, pancreatic cancer, glioblastoma, sarcoma, desmoid tumors, adenoid cystic carcinoma (ACC), colorectal cancer, prostate cancer, or medulloblastoma in a patient by administering simultaneously, separately, or sequentially, 4,4,4-trifluoro-N-[(IS)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof.

22 Claims, No Drawings

(56) References Cited

FOREIGN PATENT DOCUMENTS

WO    WO 2019/090364    5/2019

OTHER PUBLICATIONS

Belyea et al., "Inhibition of the Notch-Hey1 Axis Blocks Embryonal Rhabdomyosarcoma Tumorigenesis," Clin Cancer Res, (2011) 17(23): 7324-7336.

Bender et al., "Novel inhibitor of Notch signaling for the treatment of cancer" (2013) Cancer Res 73(8 Supplement):1131.

Choi et al., "Correlation of computed tomography and positron emission tomography in patients with metastatic gastrointestinal stromal tumor treated at a single institution with imatinib mesylate: proposal of new computed tomography response criteria," J. Clin. Oncol., (2007) 25(13): 1753-1759.

Chou et al., "Quantitative analysis of dose-effect relationships: the combined effects of multiple drugs or enzyme inhibitors," Adv. Enzyme Regul., (1984) 22: 27-55.

Clinical Trial Identifier NCT/02079636. Updated Feb. 3, 2016. Retrieved from https://clinicaltrials.gov/archive/NCT02079636/2016_02_03.

Clinical Trial Identifier NCT02784795. Updated May 26, 2016. Retrieved from https://clinicaltrials.gov/archive/NCT02784795/2016_05_26.

Cullion et al., "Targeting the Notch1 and mTOR pathways in a mouse T-ALL model," Blood (2009) 113:6172-6181.

Database WPI, Week 201156, Thomas Scientific, London, GB; AN 2011-J01934, XP002771616, CN 102 085 372 (Inst Basic Medical Sci Chinese Acad Medi), Jun. 8, 2011 abstract.

Eisenhauer et al., "New response evaluation criteria in solid tumours: revised RECIST guideline (version 1.1)," European Journal of Cancer, (2009) 45: 228-247.

Gadducci et al., "Pharmacological treatment for uterine leiomyosarcomas", Expert Opin Pharmacother (2014) 16(3):335-346.

Grabher et al., "Notch 1 activation in the molecular pathogenesis of T-cell acute lymphoblastic leukaemia," Nature Review Cancer, (2006) (6):347-359.

Gutierrez et al., "NOTCH and PI3K-AKT Pathways Intertwined," Cancer Cell (2007) 12:411-413.

Hill et al., "Gamma secretase inhibition increase recognition of multiple myeloma by BCMA-specific chimeric antigen receptor modified T cells," J Immunotherapy of Cancer (2017) 5(S2):5-6.

Holford et al., "Understanding the Dose-Effect Relationship," Clin. Pharmacokinet.(1981) 6: 429-453.

Joshi et al., "Notch signaling mediates G1/S cell-cycle progression in T cells via cyclin D3 and its dependent kinases," Blood, (2009) 113(8): 1689-1698.

Lipson et al., "Durable Cancer Regression Off-treatment and Effective Reinduction Therapy with an Anti-PD-1 Antibody," Clin Cancer Res (2013) 19(2):462-468.

Loewe et al., "Effect of combinations: Mathematical basis of problem," Arch. Exp. Pathol. Pharmacol., (1926) 114: 313-326.

Massard et al., "First-in-human study of LY3039478, a Notch signaling inhibitor in advanced or metastatic cancer," J Clin Oncol (2015) 33(15_suppl):2533.

Oken et al., "Toxicity and response criteria of the Eastern Cooperative Oncology Group," Am. J. Clin. Oncol., (1982) 5: 649-655.

Palomero et al., "Oncogenic NOTCH1 Control of MYC and PI3K: Challenges and Opportunities for Anti-NOTCH1 Therapy in T-Cell Acute Lymphoblastic Leukemias and Lymphomas," Clin. Cancer Res. (2008) 14(17):5314-5317.

Park et al., "Notch3 Gene Amplification in Ovarian Cancer," Cancer Research, (2006) 66: 6312-6318.

Rangathan et al., "Notch signalling in solid tumours: a little bit of everything but not all the time," Nature Review Cancer, (2011) 11:338-351.

Rao et al., "Inhibition of NOTCH Signaling by Gamma Secretase Inhibitor Engages the RB Pathway and Elicits Cell Cycle Exit in T-Cell Acute Lymphoblastic Leukemia Cells," Cancer Res., (2009) 69(7): 3060-3068.

Robert-Moreno et al., "The notch pathway positively regulates programmed cell death during erythroid differentiation," Leukemia, (2007) 21: 1496-1503.

Roma et al., "Notch Pathway Inhibition Significantly Reduces Rhabdomyosarcoma Invasiveness and Mobility In Vitro," Clin Cancer Res, (2011) 17(3): 505-513.

Rosati et al., "Constitutively activated Notch signaling is involved in survival and apoptosis resistance of B-CLL cells," Blood, (2009) 113: 856-865.

Sekiya et al., "Intrahepatic cholangiocarcinoma can arise from Notch-mediated conversion of hepatocytes," J Clin Invest, (2012) 122(11): 3914-3918.

Shepard et al., "PI3K/mTOR inhibition upregulates NOTCH-MYC signalling leading to an impaired cytotoxic response," Leukemia (2013) 27:650-660.

Sliwa et al. "Hyperexpression of NOTCH-1 is found in immature acute myeloid leukemia." Int J Clin Exp Pathol, (2014) 7(3)): 882-889.

Takebe et al., "Targeting Notch signaling pathway in cancer: Clinical development advances and challenges," Pharmacol Ther (2014) 141(2):140-149.

Tejada et al., "The challenge of targeting Notch in hematologic malignancies," Frontiers in Pediatrics (2014) 2:1-8.

Villanueva et al., "Notch Signaling is Activated in Human Hepatocellular Carcinoma and Induces Tumor Formation in Mice," Gastroenterology, (2012) 143: 1660-1669.

Wang et al., "Hedgehog and Notch Signaling Regulate Self-Renewal of Undifferentiated Pleomorphic Sarcomas," Cancer Res, (2012) 72: 1013-1022.

Wen et al., "Updated Response Assessment Criteria for High-Grade Gliomas: Response Assessment in Neuro-Oncology Working Group," J. Clin. Oncol., (2010) 28(11): 1963-1972.

Weng et al., "Activating mutations of NOTCH1 in human T cell acute lymphoblastic leukemia," Science, (2004) 306(5694):269-271.

Westhoff et al., "Alterations of the Notch pathway in lung cancer," PNAS, (2009) 106: 22293-22298.

Worcester, "GSI inhibition may boost BCMA CAR T-cell therapy efficacy in myeloma," Hematology News. Published on Nov. 27, 2017. Retrieved on https://www.mdedge.eom/hematology-oncology/article/152733/multiple-myeloma/gsi-inhibition-may-boost-bcma-car-t-cell-therapy.

Wu et al., "Clinicopathological significance of aberrant Notch receptors in intrahepatic cholangiocarcinoma," Int J Exp Pathol, (2014) 7(6): 3272-3279.

Yoon et al., "Clinicopathological significance of altered Notch signaling in extrahepatic cholangiocarcinoma and gallbladder carcinoma," World J Gastroenterol, (2011) 17(35): 4023-4030.

Yuen et al., "Abstract CT048: Population pharmacokinetics and pharmacodynamics for an oral Notch inhibitor, LY3039478, in the first-in-man study," Cancer Research (2016) 76(14):CT048.

"Chemotherapy of Neoplastic Diseases," in Goodmann & Gilman's Manual of Pharmacology and Therapeutics (2008) Chapter 51.

Jundt et al., "Activated Notch 1 signaling promotes tumor cell proliferation and survival in Hodgkin and anaplastic large cell lymphoma," Blood (2002) 99:3398-3403.

Kandoth et al., "Mutational landscape and significance across 12 major cancer types," Nature (2013) 502(7471):333-339.

Lewis et al., "Catalytic site-directed gamma-secretase complex inhibitors do not discriminate pharmacologically between Notch S3 and beta-APP cleavages," Biochemistry (2003) 42(24):7580-7586.

Martin-Liberal, "Leiomyosarcoma: Principles of management, Intractable & rare disease research," (2013) 2(4): 127-129.

Mathieu et al., "Notch signaling regulates PD-1 expression during CD8+ T-cell activation," Immunology and Cell Biology, (2013) 91: 82-88.

Pardoll, "The blockade of immune checkpoints in cancer immunotherapy," Nature (2012) 12:252-264.

(56) References Cited

OTHER PUBLICATIONS

Pant et al., Journal of Clinical Oncology, 2012; 30(15_suppl):3008-3008) (Year: 2012).
Sahebjam et al., "A Phase I study of the combination of ro4929097 and cediranib in patients with advanced solid tumours (PJC-004/NCI 8503)" Brit J of Cancer (2013) 109:943-949.
Seow et al., "Advances in Targeted and Immunobased Therapies for Colorectal Cancer in the Genomic Era," Onco Targets Ther. (2016) 9: 1899-1920.
Smith et al., "A phase I dose escalation and expansion study of the anticancer stem cell agent demcizumab (Anti-DLL4) in patients with previously treated solid tumors," Clin Cancer Re (2014) 20(24):6295-303
Wooldridge et al., "Corticosteroids in Advanced Cancer," Oncology (2001) 15(2):225-236.

\* cited by examiner

COMBINATION THERAPY WITH NOTCH AND CDK4/6 INHIBITORS FOR THE TREATMENT OF CANCER

CROSS REFERENCE TO RELATED APPLICATIONS

This application is a U.S. National Stage Application under 35 U.S.C. § 371 of International Application No. PCT/US2017/026134, filed internationally on Apr. 5, 2017, which claims priority to and the benefit of U.S. Provisional Application No. 62/321,311 filed Apr. 12, 2016.

The present invention relates to combination cancer therapy with 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof (Compound A) and N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof (Compound B) and to methods of using combinations to treat acute myelogenous leukemia, chronic myelogenous leukemia, breast cancer, ovarian cancer, malignant melanoma, lung cancer, pancreatic cancer, glioblastoma, sarcoma, desmoid tumors, adenoid cystic carcinoma (ACC), colorectal cancer, prostate cancer, or medulloblastoma.

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, is a Notch pathway signaling inhibitor compound. Notch signaling plays an important role during development and tissue homeostasis. Dysregulation of Notch signaling due to mutation, amplification, or overexpression of ligands and/or receptors, is implicated in a number of malignancies. Inhibition of Notch signaling is a potential target for the development of cancer therapeutics. Compound A and methods of making and using this compound, including for the treatment of T-cell acute lymphoblastic leukemia, acute lymphoblastic leukemia, acute myelogenous leukemia, chronic myelogenous leukemia, erythroleukemia, breast cancer, ovarian cancer, melanoma, lung cancer, pancreatic cancer, glioblastoma, colorectal cancer, head and neck cancer, cervical cancer, prostate cancer, liver cancer, squamous cell carcinoma (oral), skin cancer and medulloblastoma are disclosed in WO 2013/016081. Compound A is being investigated in a phase 1 clinical trial and expansion cohorts having a defined molecular pathway alteration, or a tissue based malignant tumor, and in a clinical trial in patients with T-cell acute lymphoblastic leukemia or T-cell lymphoblastic lymphoma (T-ALL/T-LBL).

N-[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine (abemaciclib) is an inhibitor of cyclin dependent kinases 4 and 6 (CDK4/6). Many mammalian tumors, including human tumors, acquire alterations, which can lead to activation of cyclin-dependent kinases (CDKs) CDK4 and CDK6. These alterations include mutations that directly activate CDK4 and CDK6, gene amplifications, which increase expression of various protein activators such as cyclin D, as well as genetic losses, which reduce expression of protein inhibitors such as p16. These various mechanism as well as loss of retinoblastoma (Rb) can lead to an enhanced proliferative potential by decreasing dependency on external growth factors and mitogenic signaling pathways, which are required to stimulate growth under normal conditions.

Abemaciclib and methods of making and using this compound including for the treatment of colorectal cancer, breast cancer, ovarian cancer, lung cancer, especially non small cell lung cancer (NSCLC), prostate cancer, melanoma, including malignant melanoma and metastatic malignant melanoma, pancreatic cancer, glioblastoma, medulloblastoma, mantel cell lymphoma, chronic myeloid leukaemia (CML), and acute myeloid leukaemia (AML) are disclosed in WO2010/075074. Compound B is being investigated in clinical trials for treating metastatic breast cancer, metastatic breast cancer in combination with fulvestrant, KRAS mutant non-small cell lung cancer (NSCLC), metastatic breast cancer in combination with letrozole or anastrozole, and mantle cell lymphoma.

Combinations of a CDK4 and CDK6 inhibitor and a Notch signaling pathway inhibitor have been contemplated in the art, Joshi et al., *Blood,* 2009, 113(8): 1689-1698; Rao et al., *Cancer Res.,* 2009, 69(7): 3060-3068.

Despite existing treatment options for patients with cancer, there continues to be a need for new and different therapies affording one or both of enhanced efficacy and lower toxicity in treatment regimens.

It is believed the present invention provides beneficial therapeutic effects from the combined activity of Compound A and Compound B as compared to the therapeutic effects provided by either agent alone.

One aspect of the present invention provides a method of treating acute myelogenous leukemia, chronic myelogenous leukemia, breast cancer, ovarian cancer, malignant melanoma, lung cancer, pancreatic cancer, glioblastoma, sarcoma, desmoid tumors, adenoid cystic carcinoma (ACC), colorectal cancer, prostate cancer, or medulloblastoma in a patient, comprising administering to a patient in need of treatment an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and an effective amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof.

A further aspect of the present invention provides a method of treating lung cancer in a patient comprising administering to a patient in need of treatment an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and an effective amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof.

Another aspect of the present invention provides a method of treating acute myelogenous leukemia, chronic myelogenous leukemia, breast cancer, ovarian cancer, malignant melanoma, lung cancer, pancreatic cancer, glioblastoma, sarcoma, desmoid tumors, adenoid cystic carcinoma (ACC), colorectal cancer, prostate cancer, or medulloblastoma in a patient, comprising administering to a patient in need of treatment, simultaneously, separately, or sequentialy, an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and an effective amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof.

A further aspect of the present invention provides a method of treating lung cancer in a patient, comprising administering to a patient in need of treatment, simultaneously, separately, or sequentialy, an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and an effective amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof.

Another aspect of the present invention provides a compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof; and a compound N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof; for simultaneous, separate, or sequential use in the treatment of acute myelogenous leukemia, chronic myelogenous leukemia, breast cancer, ovarian cancer, malignant melanoma, lung cancer, pancreatic cancer, glioblastoma, sarcoma, desmoid tumors, adenoid cystic carcinoma (ACC), colorectal cancer, prostate cancer, or medulloblastoma.

A further aspect of the present invention provides a compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof; and a compound N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof; for simultaneous, separate, or sequential use in the treatment of lung cancer.

A further aspect of the present invention provides: use of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof for the manufacture of a medicament; and use of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof for the manufacture of a medicament; for the simultaneous, separate, or sequential treatment of acute myelogenous leukemia, chronic myelogenous leukemia, breast cancer, ovarian cancer, malignant melanoma, lung cancer, pancreatic cancer, glioblastoma, sarcoma, desmoid tumors, adenoid cystic carcinoma (ACC), colorectal cancer, prostate cancer, or medulloblastoma.

Another aspect of the present invention provides: use of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof for the manufacture of a medicament; and use of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof for the manufacture of a medicament; for the simultaneous, separate, or sequential treatment of lung cancer.

A further aspect of the present invention is a commercial package comprising a separate composition of each therapeutic agent, or a combination of the therapeutic agents of the present invention, together with instructions for simultaneous, separate or sequential administration for use in treating acute myelogenous leukemia, chronic myelogenous leukemia, breast cancer, ovarian cancer, malignant melanoma, lung cancer, pancreatic cancer, glioblastoma, sarcoma, desmoid tumors, adenoid cystic carcinoma (ACC), colorectal cancer, prostate cancer, or medulloblastoma.

A still further aspect of the present invention is a commercial package comprising a separate composition of each therapeutic agent, or a combination of the therapeutic agents of the present invention, together with instructions for simultaneous, separate or sequential administration for use in treating lung cancer.

The compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, (Compound A) has the CAS registry number 142138-81-4. Alternatively, the compound may be named: N-[(1S)-2-[[(7S)-6,7-dihydro-5-(2-hydroxyethyl)-6-oxo-5H-pyrido[3,2-a][3]benzazepin-7-yl]amino]-1-methyl-2-oxoethyl]-4,4,4-trifluorobutanamide. Other names may be used to unambiguously identify Compound A.

The compound N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, (Compound B) has the CAS registry number 1231929-97-7. The generic name for the compound is abemaciclib. Alternative compound names include 2-pyrimidinamine, N-[5-[(4-ethyl-1-piperazinyl)methyl]-2-pyridinyl]-5-fluoro-4[4-fluoro-2-methyl-1-(1-methylethyl)-1H-benzimidazol-6-yl]-, 1-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, and [5-((4-ethylpiperazin-1-yl)methyl)pyridin-2-yl]-5-fluoro-4-(4-fluoro-1-isopropyl-2-methyl-1H-benzo[d]imidazole-6-yl)pyrimidin-2-amine. Other names may be used to unambiguously identify Compound B.

As used herein, the term "patient" refers to a mammal, preferably a human.

"Therapeutically effective amount" or "effective amount" means the dosage of Compound A, or pharmaceutically acceptable salt or hydrate thereof, or pharmaceutical composition containing Compound A, or pharmaceutically acceptable salt or hydrate thereof, and the dosage of Compound B, or pharmaceutically acceptable salt thereof, or pharmaceutical composition containing Compound B, or pharmaceutically acceptable salt thereof, necessary to inhibit tumor cell growth and eliminate or slow or arrest the progression of the cancer in a patient. Anticipated dosages of Compound A, or a pharmaceutically acceptable salt thereof, are in the range of 2.5 mg/patient to 75 mg/patient T.I.W. Anticipated dosages of Compound B, or a pharmaceutically acceptable salt or hydrate thereof, are in the range of 75 mg to 200 mg twice per day (B.I.D.) dosing. Preferred dosages of Compound A, or a pharmaceutically acceptable salt or hydrate thereof, are anticipated to be in the range of 5 mg to 50 mg T.I.W. and Compound B, or a pharmaceutically acceptable salt thereof, in the range of 100 mg to 150 mg twice per day. The exact dosage required to treat a patient and the length of treatment time will be determined by a physician in view of the stage and severity of the disease as well as the specific needs and response of the individual patient. The dosing administration may be adjusted to provide a more optimal therapeutic benefit to a patient and to manage or ameliorate any drug related toxicities. Alternative dosing schedules such as once per day (QD), twice per day (B.I.D.), three times a day (T.I.D.); dosing once per day every other day (Q2D); once per day every other day over a five day period followed by two days without dosing (T.I.W.); or every third day (Q3D) may be appropriate for each of Compound A and Compound B.

A combination therapy of the present invention is carried out by administering to a lung cancer patient, or other named cancer patient requiring treatment, an effective amount of Compound A, or a pharmaceutically acceptable salt or hydrate thereof, once per day every other day over five days and two days without dosing each week (7-days) over a 14-28 day cycle and Compound B, or a pharmaceutically acceptable salt thereof, twice per day over a 14-28 day cycle.

The terms "treatment," "treat," and "treating," are meant to include the full spectrum of intervention for the cancer from which the patient is suffering, such as administration of Compounds A and B to alleviate, slow, stop, or reverse one or more of the symptoms and to delay, stop, or reverse progression of the cancer even if the cancer is not actually eliminated.

Compound A or a pharmaceutically acceptable salt or hydrate thereof, is preferably formulated as a pharmaceutical composition using a pharmaceutically acceptable carrier and administered by a variety of routes. Preferably, such compositions are for oral administration. Compound B, or a pharmaceutically acceptable salt thereof, is preferably formulated as a pharmaceutical composition using a pharmaceutically acceptable carrier and administered by a variety of routes. Preferably, such compositions are for oral administration. Such pharmaceutical compositions and processes for preparing them are well known in the art. See, for example, HANDBOOK OF PHARMACEUTICAL EXCIPIENTS, 5$^{th}$ edition, Rowe et al., Eds., Pharmaceutical Press (2006); and REMINGTON: THE SCIENCE AND PRACTICE OF PHARMACY (Troy, et al., Eds., 21$^{st}$ edition, Lippincott Williams & Wilkins (2006).

Each of Compound A and Compound B are capable of reaction with a number of inorganic and organic counterions to form pharmaceutically acceptable salts. Such pharmaceutically acceptable salts and common methodology for preparing them are well known in the art. See, for example, P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

The efficacy of the combination treatment of the invention can be measured by various endpoints commonly used in evaluating cancer treatments, including but not limited to, tumor regression, tumor weight or size shrinkage, time to progression, overall survival, progression free survival, overall response rate, duration of response, and inhibition of metatstatic spread without tumor regression.

The terms "combination" and "pharmaceutical combination" refer to either: 1) a fixed dose combination in one dosage unit form; or 2) a non-fixed dose combination, optionally packaged together for combined administration.

The term "simultaneous" administration means the administration of each of Compound A and Compound B to a patient in a single action such as where the two agents are incorporated into a single dosage form for administration (fixed dose combination) and where each of Compound A and Compound B are administered independently at substantially the same time or separately within time intervals that allows Compounds A and B to show a cooperative therapeutic effect.

The term "separate" administration means the administration of each of Compound A and Compound B to a patient from non-fixed dose combination dosage forms simultaneously, substantially concurrently, or sequentially in any order. There may be a specified time interval for administration of each Compound.

The term "sequential" administration means the administration of each of Compound A and Compound B to a patient from non-fixed (separate) dosage forms in separate actions. The two administration actions may be linked by a specified time interval. For example, administering Compound A daily and administering Compound B every other day.

The phrase "in combination with" includes the simultaneous, separate, and sequential administration of each of Compound A and Compound B to a cancer patient in need of treatment.

The term "co-administration" or "combined administration" encompasses the administration of the therapeutic agents to a single patient, and include treatment regimens in which the agents may be administered by different routes of administration or at different times.

The beneficial action of two therapeutic agents producing an effect in a single patient which is greater than the simple additive effects of each agent administered alone may be calculated, for example, using suitable methods known in the art such as the Sigmoid-Emax equation (Holford and Scheiner, *Clin. Pharmacokinet.*, 1981, 6: 429-453), the equation of Loewe additivity (Loewe and Muischenk, *Arch. Exp. Pathol. Pharmacol.*, 1926, 114: 313-326), the median-effect equation (Chou and Talalay, *Adv. Enzyme Regul.*, 1984, 22: 27-55), or the Bliss Independence method. Each equation, or analysis, may be applied to experimental data to generate a corresponding graph to aid in assessing the effects of a drug combination. The corresponding graphs associated with the equations include the concentration-effect curve, isobologram curve and combination index curve.

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenviroments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

The nature of cancer, as noted, is multifactorial. Under appropriate circumstances, therapeutic agents with different mechanisms of action may be combined. However, only considering a combination of therapeutic agents having different modes of action does not necessarily lead to combinations with advantageous effects. Specific therapeutic agents affording demonstrated beneficial effects (therapeutic effect such as enhanced efficacy and/or lower toxicity) compared with monotherapy of each of the therapeutic agents, independently, is preferred.

The combination of the present invention is particularly suitable for the treatment of lung cancer patients who have failed standard therapy. This includes patients having lung cancer showing resistance to monotherapy or showing resistance to combinations different than the present invention.

The terms "Complete Response" (CR), "Partial Response" (PR), "Progressive Disease" (PD), "Stable Disease" (SD), "Objective Response" (OR) are used consistent with definitions according to RECIST v1.1, Eisenhauer et al., *European Journal of Cancer*, 2009, 45, 228-247.

The term "time to disease progression" (TTP) refers to the time, generally measured in weeks or months, from the time of initial treatment, until the cancer progresses (see RECIST v1.1 definition for progressive disease) which is at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. The appearance of one or more new lesions is also considered progression. Such progression is evaluated by a clinician.

The term "extending TTP" refers to increasing the time to disease progression in a treated patient relative to i) an untreated patient, or ii) a patient a patient treated with less than both of Compound A and Compound B.

The term "survival" refers to the patient remaining alive, and includes overall survival as well as progression free survival.

The term, "overall survival" refers to the patient remaining alive for a defined period of time, such as 1 year, 5 years, etc. from the time of diagnosis or treatment.

The term, "progression free survival" refers to the patient remaining alive, without the cancer progressing.

As used herein, the term "extending survival" is meant increasing overall or progression free survival in a treated patient relative to i) an untreated patient, ii) a patient treated with less than both of Compound A and Compound B, or iii) a control treatment protocol. Survival is monitored for a defined period of time, such as one month, six months, 1 year, 5 years, or 10 years, etc., following the initiation of treatment or following the initial diagnosis of cancer.

The term "primary tumor" or "primary lesion" is meant the original cancer and not a metastatic tumor or lesion located in another tissue, organ, or location in the patient's body.

In one embodiment, the dose of Compound A is escalated until the Maximum Tolerated Dosage is reached, and Compound B of the present invention is administered with a fixed dose. Alternatively, Compound A may be administered in a fixed dose and the dose of Compound B may be escalated. Each patient may receive doses of Compound A and/or Compound B either daily or intermittently. The efficacy of the treatment may be determined in such studies, e.g., after 12, 18 or 24 weeks by evaluation of symptom scores every 6 weeks.

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, may be prepared by the procedures described in WO 2013/016081.

N-[5-(4-Ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine or a pharmaceutically acceptable salt thereof, may be prepared by the procedures disclosed in WO2010/075074.

The following Biological Examples illustrate the activity of each of Compound A alone, Compound B alone and the combination of Compound A and Compound B.

BIOLOGICAL EXAMPLE 1

The non-small cell lung cancer (NSCLC) lines NCI-H441 (ATCC® as HTB-174) and NCI-H2122 (ATCC® as CRL-5985) are grown in RPMI-1640 medium supplemented with 2 mM L-glutamine, 10 mM HEPS, 1 mM sodium pyruvate, 4500 mg/L glucose, 1500 mg/L sodium bicarbonate, and 10% fetal bovine serum (FBS) at 37° C. in 5% $CO_2$ with humidity in the atmosphere. The cells are subcultured according to ATCC procedures and treated with increasing concentrations of abemaciclib mesylate (Compound B) either in the presence or absence of 1 µM of Compound A. The growth of the cells is quantified 48 hours later by a CellTiter-Glo assay (Promega). Growth inhibition at each concentration is calculated and $IC_{50}$ values are determined from the 4-parameter concentration-response curves. The growth curves indicate that the combination modestly enhanced growth inhibition in one (H2122) but not both cell lines. NCI-H4441: Compound B $IC_{50}$=0.97 µM; Compound B+Compound A $IC_{50}$=0.78 µM. NCI-H2122: Compound B $IC_{50}$=0.45 µM; Compound B+Compound A $IC_{50}$=0.14 µM.

Time Course Study: NCI-H441 and NCI-H2122 NSCLC cell lines are treated for 4 or 24 hours with 1 µM of Compound A and harvested to evaluate effects on cell cycle biomarker expression which includes the cell cycle inhibitors p21 and p27 as well as markers for cell cycle progression including phospho-histone H3 (pHH3) (a marker for M-phase), Topo 2A (a marker for S-phase), phospho-_ser780-RB (a marker for G1 and, as well as, for CDK4/6 inhibition) and cyclin Dl. Marginal reductions of pHH3, Topo2A, pRB and total RB are observed in H2122 cells after 24 hours of treatment which indicates possible inhibition of cell cycle. These data correlate with the observations in the H2122 cells for growth inhibition where the combination had a modest impact on cell growth.

Concentration-response study: H2122 cells are treated with various concentrations (0.05, 0.1, 0.2, 0.4, and 0.8 µM) of Compound B in the presence or absence of 1 µM of Compound A where both compounds are added to the cultures simultaneously. Cells are harvested after 24 hours of treatment and evaluated for expression of various cell cycle biomarkers by immunoblotting. As a selective CDK4/6 inhibitor, Compound B shows concentration-dependent inhibition of pRB (phospho-ser780-Rb), total RB, Topo IIa and pHH3. RB is the direct kinase target of CDK4/6 so inhibition of pRB provides a direct measure of CDK4/6 inhibition. The inhibition of Topo IIA and pHH3 are indicative of the inhibition of cell cycle progression through S and M phases of the cell cycle, respectively. The results indicate that Compound A slightly increases the sensitivity of these biomarkers to inhibition by Compound B. Compound A alone at 1 µM has no effect on the expression of these biomarkers. The same study is carried out in the H441 cell line. In this cell line, there is no change in cell cycle biomarker expression when Compound B monotherapy is compared to combination treatment with Compound A. This is consistent with the cell growth studies which showed the combination of Compound A did not enhance growth inhibition by Compound B.

Concentration-response study: H2122 cells are treated with various concentrations (0.05, 0.1, 0.2, 0.4, and 0.8 µM)

of Compound B in the presence or absence of 1 μM of Compound A where Compound A is added to the cultures 1 day before Compound B. Cells are harvested 24 hours after the addition and evaluated for expression of various cell cycle biomarkers by immunoblotting. As a selective CDK4/6 inhibitor, Compound B shows concentration-dependent inhibition of pRB (phospho-ser780-Rb), total RB, Topo IIa and pHH3. RB is the direct kinase target of CDK4/6 so inhibition of pRB provides a direct measure of CDK4/6 inhibition. The inhibition of Topo IIA and pHH3 are indicative of the inhibition of cell cycle progression through S and M phases of the cell cycle, respectively. The results indicate that Compound A slightly increases the sensitivity of these biomarkers to inhibition by Compound B. Compound A alone at 1 μM has no effect on the expression of these biomarkers. These data are not different from the studies in which both compounds were added simultaneously.

BIOLOGICAL EXAMPLE 2

NCI-H2122 is a human adenocarcinoma non-small cell lung cancer cell line (ATCC® as CRL-5985). The cells are grown in culture media at 37° C. in 5% $CO_2$ with humidity in the atmosphere. Cell culture media for NCI-H2122 is RPMI-1640 with 2 mM L-glutamine, 10 mM 2-[4-(2-hydroxyethyl)piperazin-1-yl]ethanesulfonic acid (HEPES), 1 mM sodium pyruvate, 4500 mg/L glucose, 1500 mg/L sodium bicarbonate, and 10% fetal bovine serum (FBS).

To evaluate in vivo efficacy $5 \times 10^6$ NCI-H2122 cells in a 1:1 Matrigel® mix (0.2 mL volume) are implanted by subcutaneous injection in the hind leg of 6-8 weeks of age athymic nude female mice (Harlan Laboratories). Just before implantation animals are irradiated (450 Total Body Irradiation). Mice are fed ad libitum on normal chow. Treatment is initiated with oral administration (gavage) of Compound A in 1% sodium carboxymethylcellulose (Na-CMC) in 0.25% Tween®-80, or Compound B in 1% hydroxyethyl cellulose (HEC) in phosphate buffer pH 2.0 or their respective vehicle in 0.2 mL volume when tumor size reaches to 150±50 mm³. Compound A is administered at 5 or 8 mg/kg on a Wednesday, Friday, and Monday schedule (TIW) for 2 weeks and Compound B is administered at 25 or 50 mg/kg daily for 14 days.

Tumor growth and body weight are monitored over time to evaluate efficacy and signs of toxicity. Bidimensional measurements of tumors are performed twice a week and tumor volumes are calculated based on the following formula: (Tumor Volume)=[(L)×(W2)×(Π/6)] where L is mid-axis length and W is mid-axis width. Tumor volume data are transformed to a log scale to equalize variance across time and treatment groups. The log volume data are analyzed with a two-way repeated measures analysis of variance by time and treatment using the MIXED™ procedures in SAS™ software (version 8.2). The correlation model for the repeated measures is spatial power. Least squares means from the repeated measures analysis, anti-logged to the tumor volume scale, are shown in Table 1. P-values for comparing each pair of groups on study day 27 are shown in Table 2. Test Groups are:

1: 1% HEC in 25 mM Phosphate Buffer, pH 2, QD×14, PO/1% CMC/0.25% Tween 80/0.05% Antifoam, /W-F-M×2, PO
3: Compound B, 50 mg/kg, QD×14, PO
4: Compound A, 5 mg/kg, W-F-M×2, PO
5: Compound A, 8 mg/kg, W-F-M×2, PO
7: Compound B, 50 mg/kg, QD×14, PO/Compound A, 5 mg/kg, W-F-M×2, PO
8: Compound B, 50 mg/kg, QD×14, PO/Compound A, 8 mg/kg, W-F-M×2, PO Group 7 and a Group 9 were combined and labelled group 7, because they received the same treatment regimen contrary to testing procedures. Group 6 was terminated early due to infection and did not provide evaluable results. Group 2 is not shown as it was Compound B monotreatment at the same treatment regimen as Compound B in Group 6 combination treatment.

Human NCI-H2122 Xenograft

TABLE 1

| | Geometric Mean | | | | | | |
|---|---|---|---|---|---|---|---|
| | Study Days | | | | | | |
| Group | 6 | 9 | 13 | 16 | 20 | 23 | 27 |
| 01 | 86.43 | 129.64 | 203.02 | 402.98 | 755.22 | 800.27 | 955.37 |
| 03 | 136.94 | 188.32 | 191.75 | 321.32 | 376.59 | 489.72 | 491.92 |
| 04 | 110.18 | 129.04 | 189.14 | 289.03 | 447.05 | 585.69 | 761.24 |
| 05 | 127.60 | 165.23 | 199.00 | 301.93 | 492.37 | 481.31 | 570.39 |
| 07 | 102.19 | 138.73 | 196.00 | 246.20 | 254.14 | 266.66 | 211.81 |
| 08 | 124.82 | 173.30 | 191.98 | 256.87 | 306.45 | 276.42 | 293.62 |

TABLE 2

| Between Group P-Values (Repeated Measures ANOVA) | | | | | | |
|---|---|---|---|---|---|---|
| Group | 3 | 4 | 5 | 7 | 8 | Study Day |
| 1 | <0.001 | 0.212 | 0.005 | <0.001 | <0.001 | 27 |
| 3 | | 0.017 | 0.415 | <0.001 | 0.006 | 27 |
| 4 | | | 0.113 | <0.001 | <0.001 | 27 |
| 5 | | | | <0.001 | <0.001 | 27 |
| 7 | | | | | 0.141 | 27 |

Table 2 shows the combination of Compound B at 50 mg/kg and Compound A at 5 mg/kg (Group 7), in this test, demonstrated statistically significant tumor growth inhibition results over each of Compound B at 50 mg/kg (Group 3) and Compound A at 5 mg/kg (Group 4) alone. Table 5 also shows the combination of Compound B at 50 mg/kg and Compound A at 8 mg/kg (Group 8), in this test, demonstrated statistically significant tumor growth inhibition results over each of Compound B at 50 mg/kg (Group 3) and Compound A at 8 mg/kg (Group 5) alone.

Combination Analysis

Using the repeated measures analysis previously described, a contrast statement is used to test for an interaction effect on study day 27, using the two specific treatments that were combined (Group 7). This test is statistically significant for Group 7 with p=0.026, demonstrating better than additive, or synergistic activity, since the estimated mean tumor volume in the combination group (212 mm$^3$) is less than the expected additive tumor volume per the Bliss Independence method (492×761/955=392 mm$^3$).

Clinical Evaluation

A study of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate in combination with N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, in patients with advanced or metastatic solid cancer tumors.

Study Design

This study is a multicenter, nonrandomized, open-label study consisting of a dose escalation phase in patients with advanced/metastatic cancer from a variety of solid tumors followed by a dose confirmation phase in specific tumor types. In the dose escalation phase, eligible patients will receive Compound A given orally, T.I.W. in combination with a cyclin-dependent kinase 4 and 6 (CDK4/6) inhibitor (abemaciclib; Compound B) given orally every 12 hours, on a 28-day cycle. A single dose of abemaciclib will also be given on Day 1 during a 3-day lead-in period (dose-escalation phase only) for PK evaluation. In the dose-confirmation phase approximately 15 patients with metastatic breast cancer that have mutations, amplification, or gene expression alterations related to Notch pathway signaling will be treated.

Study Objectives

The primary objective of this study is to determine the recommended Phase 2 dose of Compound A in combination with abemaciclib (Compound B) anticancer agent.

The secondary objectives of the study are to characterize the safety and toxicity profile of Compound A in combination with Compound B as assessed by National Cancer Institute's (NCI) Common Terminology Criteria for Adverse Events (CTCAE) v4.0; to estimate the PK parameters of abemaciclib and its major active metabolites 5-fluoro-4-[4-fluoro-2-methyl-1-(1-methylethyl)-1H-benzimidazol-6-yl]-N-[5-(piperazin-1-ylmethyl)pyridin-2-yl]pyrimidin-2-amine and {6-[2-({5-[(4-ethylpiperazin-1-yl)methyl]pyridin-2-yl}amino)-5-fluoropyrimidin-4-yl]-4-fluoro-1-(propan-2-yl)-1H-benzimidazol-2-yl}methanol in combination with Compound A; to document any antitumor activity observed with Compound A in combination with abemaciclib; and to assess duration of response and progression free survival (PFS).

Exploratory objectives are to explore pharmacodynamic (PD) effects of Compound A on biomarkers indicative of Notch activity or abemaciclib; to explore the utility of positron emission tomography (PET) scan to assess treatment effect with Compound A in combination with abemaciclib; to explore predictive biomarkers related to induction of cytochrome P450 (CYP) enzymes, such as cortisol and 6β-hydroxycortisol; and to evaluate tumor tissue and blood for biomarkers related to the Notch signaling pathway and drug target pathways, immune functioning, mechanism of action of study drug(s) or disease state, and their potential association with the objectives of the study.

Trial Drug 4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate, dose range 25-50 mg given orally as capsules 3 times per week (7-day week) during a 28-day cycle.

N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, dose 50 mg given orally as capsules QD during a 28-day cycle.

4,4,4-Trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide hydrate is supplied as capsules in bottles for oral consumption. These capsules should be stored at room temperature within the temperature range stated on the label.

N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, is supplied as 50 mg hypomellose capsules. These capsules should be stored at room temperature within the temperature range stated on the label.

Planned Duration of Treatment/Dosing

By nature of being a dose escalation study, data will be evaluated on an ongoing basis until the maximum tolerated dose (MTD) of the combination is determined. Dose escalation will be driven by the 3+3 method.

Each new dose level will have a minimum of 3 patients enrolled to it. If 1 patient, at any dose level, experiences a dose-limiting toxicity (DLT) within the first cycle of Compound A, then up to 3 additional patients will be enrolled at that dose level. If a DLT is observed in 2 or more patients at any dose level, dose escalation will cease and either the previous dose level will be declared the maximum tolerated dose (MTD) or, following discussions between the sponsor and investigators additional patients may be treated at intermediate doses between the previous and current dose levels.

During dose escalation, the starting dose of Compound A will be 25 mg TIW and starting dose of Compound B will be 100 mg BID. Dose escalation is scheduled to proceed according to Table 3.

TABLE 3

Dose-Escalation Scheme

| Dose Level | Compound A Dose (mg) | Compound B Dose (mg) |
|---|---|---|
| 1 | 25 | 100 BID |
| 2 | 50 | 100 BID |
| 3 | 50 | 150 BID |

Abbreviation: BID = twice daily.

Criteria for Evaluation

Safety: NCI CTCAE, version 4.0, dose-limiting toxicities (DLT).

Efficacy: Each patient will be assessed by one or more of the following radiologic tests for tumor measurement: Computed tomography (CT) scan; Magnetic resonance imaging (MRI); and PET scan (pre- and postdose). Each patient's full extent of disease will also be assessed with:

Tumor measurement by RECIST 1.1 (Eisenhauer et al., *Eur. J. Cancer*, 2009; 45(2): 228-247). For tumor measurement evaluations in patients with soft tissue sarcomas, Choi et al., *J. Clin. Oncol.*, 2007; 25(13): 1753-1759 response criteria will be used in addition to RECIST 1.1. Response Assessment in Neuro-Oncology (RANO) criteria will be used for glioblastoma patients (Wen et al., *J. Clin. Oncol.*, 2010; 28(11): 1963-1972);

Evaluation of tumor markers, if indicated;

Evaluation of performance status (Eastern Cooperative Oncology Group (ECOG); Oken et al., *Am. J. Clin. Oncol.,* 1982; 5: 649-655).

To confirm objective responses, all lesions should be radiologically assessed, and the same radiologic method used for the initial response determination should be repeated at least 4 weeks following the initial observation of an objective response, using the sample method that was used at baseline. If a patient is discontinued from the study, repeat radiology assessments may be omitted if clear clinical signs of progressive disease are present.

We claim:

1. A method of treating a cancer, comprising administering to a patient in need of such treatment an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and an effective amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof, wherein the cancer is selected from the group consisting of acute myelogenous leukemia, chronic myelogenous leukemia, breast cancer, ovarian cancer, malignant melanoma, lung cancer, pancreatic cancer, glioblastoma, sarcoma, desmoid tumors, adenoid cystic carcinoma, colorectal cancer, prostate cancer, and medulloblastoma.

2. The method of claim 1, wherein the cancer is lung cancer.

3. The method of claim 1, wherein the administering is by simultaneous administration of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof and N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof.

4. The method of claim 1, wherein the administering is by separate administration of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof and N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof.

5. The method of claim 1, wherein the administering is by sequential administration of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof and N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof.

6. The method of claim 3, wherein the cancer is lung cancer.

7. The method of claim 4, wherein the cancer is lung cancer.

8. The method of claim 5, wherein the cancer is lung cancer.

9. The method of claim 1, wherein the amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is between 2.5 mg and 75 mg.

10. The method of claim 1, wherein the amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is between 5 mg and 50 mg.

11. The method of claim 1, wherein the amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is 25 mg.

12. The method of claim 1, wherein the amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is 50 mg.

13. The method of claim 1, wherein the 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is for use once per day every other day over a five day period followed by two days without dosing (T.I.W.).

14. The method of claim 1, wherein the amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof is between 75 mg and 200 mg.

15. The method of claim 1, wherein the amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof is between 100 mg and 150 mg.

16. The method of claim 1, wherein the amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof is 100 mg.

17. The method of claim 1, wherein the amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof is 150 mg.

18. The method of claim 1, wherein the N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof is for use twice per day (B.I.D.).

19. The method of claim 1, wherein the 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof and the N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof are formulated for oral administration.

20. The method of claim 1, wherein the amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is between 2.5 mg and 75 mg; and the amount of N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof is between 75 mg and 200 mg.

21. The method of claim 2, wherein the amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is between 2.5 mg and 75 mg; and the amount of N-[5-(4-ethyl-piperazin-1-ylmethyl)-pyridin-2-yl]-[5-fluoro-4-(7-fluoro-3-isopropyl-2-methyl-3H-benzo-imidazol-5-yl)-pyrimidin-2-yl]-amine, or a pharmaceutically acceptable salt thereof is between 75 mg and 200 mg.

22. The method of claim 20, wherein the 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is for use once per day every other day over a five day period followed by two days without dosing (T.I.W.); and the N-[5-(4-ethyl-piperazin-1-ylmethyl)-pyridin-2-yl]-[5-fluoro-4-(7-fluoro-3-isopropyl-2-methyl-3H-benzoimidazol-5-yl)-pyrimidin-2-yl]-amine, or a pharmaceutically acceptable salt thereof is for use twice per day (B.I.D.).

\* \* \* \* \*